(12) United States Patent
Taranta et al.

(10) Patent No.: US 9,241,912 B2
(45) Date of Patent: Jan. 26, 2016

(54) AGROCHEMICAL FORMULATION COMPRISING ENCAPSULATED PESTICIDE

(75) Inventors: Claude Taranta, Stutensee (DE); Thomas Bork, Westhofen (DE); Tina Schroeder-Grimonpont, Rheinzabern (DE); Britta Katz, Dannstadt-Schauernheim (DE); Tatjana Sikuljak, Mannheim (DE); Simon Nord, Karlsruhe (DE); Juergen Distler, Freimersheim (DE); Richard A. Warriner, Wake Forest, NC (US); Daniel Bihlmeyer, Apex, NC (US); James Thomas Wofford, Fuquay Varina, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/978,833

(22) PCT Filed: Jan. 11, 2012

(86) PCT No.: PCT/EP2012/050327
§ 371 (c)(1),
(2), (4) Date: Jul. 9, 2013

(87) PCT Pub. No.: WO2012/095436
PCT Pub. Date: Jul. 19, 2012

(65) Prior Publication Data
US 2013/0287844 A1  Oct. 31, 2013

Related U.S. Application Data

(60) Provisional application No. 61/431,458, filed on Jan. 11, 2011.

(30) Foreign Application Priority Data

Feb. 2, 2011 (EP) .................................... 11152994

(51) Int. Cl.
*A61K 9/50* (2006.01)
*A01N 25/28* (2006.01)
*C08G 18/62* (2006.01)

(52) U.S. Cl.
CPC .............. *A61K 9/5031* (2013.01); *A01N 25/28* (2013.01); *C08G 18/6212* (2013.01)

(58) Field of Classification Search
CPC ....... A01N 25/28; A01N 25/04; A01N 53/00; C08G 2310/00
See application file for complete search history.

(56) References Cited

U.S. PATENT DOCUMENTS

| | | | |
|---|---|---|---|
| 4,056,610 A | 11/1977 | Barber et al. | |
| 4,985,064 A | 1/1991 | Redlich et al. | |
| 5,925,464 A * | 7/1999 | Mulqueen et al. | 428/402.2 |
| 6,133,197 A * | 10/2000 | Chen et al. | 504/359 |
| 2002/0136773 A1 | 9/2002 | Scher et al. | |
| 2005/0233907 A1* | 10/2005 | Nabors et al. | 504/149 |
| 2010/0041629 A1 | 2/2010 | Giessler-Blank et al. | |

FOREIGN PATENT DOCUMENTS

| | | |
|---|---|---|
| AU | 710988 | 7/1997 |
| EP | 0 611 253 | 8/1994 |
| EP | 0 619 073 | 10/1994 |
| EP | 0 747 116 | 12/1996 |
| EP | 2153889 | 2/2010 |
| JP | 09-235204 | 9/1997 |
| JP | 09-249505 | 9/1997 |
| WO | WO 95/13698 | 5/1995 |
| WO | WO 9513698 | 5/1995 |
| WO | WO 96/33611 | 10/1996 |
| WO | WO 2004/017734 | 3/2004 |
| WO | WO 2010/081480 | 7/2010 |
| WO | WO 2011017480 | 2/2011 |
| WO | WO 2012018885 | 2/2012 |

OTHER PUBLICATIONS

Lambda-Cyhalothrin (http://www.fao.org/fileadmin/templates/agphome/documents/Pests_Pesticides/JMPR/Evaluation08/Lambda-cyhalotrhin.pdf) accessed Oct. 9, 2014.*
International Search Report dated Feb. 8, 2012, prepared in International Application No. PCT/EP2012/050327.
International Preliminary Report on Patentability dated Apr. 23, 2013, prepared in International Application No. PCT/EP2012/050327.
Sieke, "Lambda-Cyhalothrin (146)", Federal Institute for Risk Assessment, Berlin, Germany, 2008, pp. 549-783, http://www.fao.org/fileadmin/templates/agphome/documents/Pests_Pesticides/JMPR/Evaluation08/Lambda-cyhalotrhin.pdf, accessed on Jan. 28, 2015.

* cited by examiner

*Primary Examiner* — Sean Basquill
*Assistant Examiner* — Andrew S Rosenthal
(74) *Attorney, Agent, or Firm* — Brinks Gilson & Lione

(57) ABSTRACT

The present invention relates to microcapsules comprising a polyurea shell and a core, which contains a pesticide, a water-immiscible solvent A and at least 5 wt % of an aprotic, polar solvent B, which has a solubility in water from 0.5 to 20 g/l at 20° C., based on the total weight of the solvents in the core. It further relates to microcapsules comprising a shell and a core, which contains a pesticide and 2-heptanone; to a method for preparing said microcapsules; to an aqueous composition comprising said microcapsules; and to a method for controlling phytopathogenic fungi and/or undesired plant growth and/or undesired attack by insects or mites and/or for regulating the growth of plants, with said microcapsules.

14 Claims, No Drawings

AGROCHEMICAL FORMULATION COMPRISING ENCAPSULATED PESTICIDE

This application is a National Stage application of International Application No. PCT/EP2012/050327, filed Jan. 11, 2012, which claims the benefit of U.S. Provisional Application No. 61/431,458, filed Jan. 11, 2011, the entire contents of which are hereby incorporated herein by reference. This application also claims priority under 35 U.S.C. §119 to European Patent Application No. 11152994.7, filed Feb. 2, 2011, the entire contents of which is hereby incorporated herein by reference.

The present invention relates to microcapsules comprising a polyurea shell and a core, which contains a pesticide, a water-immiscible solvent A and at least 5 wt % of an aprotic, polar solvent B, which has a solubility in water from 0.5 to 20 g/l at 20° C., based on the total weight of the solvents in the core. It further relates to microcapsules comprising a shell and a core, which contains a pesticide and 2-heptanone; to a method for preparing said microcapsules; to an aqueous composition comprising said microcapsules; and to a method for controlling phytopathogenic fungi and/or undesired plant growth and/or undesired attack by insects or mites and/or for regulating the growth of plants, with said microcapsules. Combinations of preferred embodiments with other preferred embodiments are within the scope of the present invention.

Microcapsules comprising a polyurea shell and a core, which contains a pesticide and solvents are known:

WO 96/33611 discloses a microcapsule containing an organic liquid comprising an UV light sensitive biologically active material and an particulate UV light protectant. Suitable solvents are for example hydrocarbons, cyclohexanone or acetophenone.

EP 0619073 discloses polyurea microcapsules encapsulating a water-immiscible pesticide. Suitable solvents in which the pesticide is dissolved are for example mineral oil or cyclohexanone.

EP 0611253 discloses polyurea capsules encapsulating a water-immiscible pesticide. Suitable solvents in which the pesticide is dissolved are for example aromatic hydrocarbons or cyclohexanone.

EP 0747116 discloses polyurea capsules comprising a pesticide and a solvent, such as aromatic hydrocarbons or ketones.

U.S. Pat. No. 4,056,610 discloses polyurea microcapsules comprising a liquid fill, which contains a pyrethroid and water immiscible organic solvents, such as aromatic hydrocarbons or higher ketones.

WO 2004/017734 discloses a microencapsulated composition, wherein the encapsulated material comprises an agrochemical, an adjuvant and a water-immiscible solvent, such as aromatic solvents, methylethylketone, isophorone or dihydroisophorone.

The state of the art has various disadvantages: there is a high tendency for crystallization of the active ingredients; the stability of the formulation is rather low within broad range of temperatures; or there either only a knock-down or only a residual efficacy. Object of the present invention was to overcome such problems.

The object was solved by microcapsules comprising a polyurea shell and a core, which contains a pesticide, a water-immiscible solvent A and at least 5 wt % of an aprotic, polar solvent B, which has a solubility in water from 0.5 to 20 g/l at 20° C., based on the total weight of the solvents in the core.

Suitable examples for water-immiscible solvent A are
a hydrocarbon solvent such a an aliphatic, cyclic and aromatic hydrocarbons (e.g. toluene, xylene, paraffin, tetrahydronaphthalene, alkylated naphthalenes or their derivatives, mineral oil fractions of medium to high boiling point (such as kerosene, diesel oil, coal tar oils));
a vegetable oil such as corn oil, rapeseed oil;
a fatty acid ester such as $C_1$-$C_{10}$-alkylester of a $C_{10}$-$C_{22}$-fatty acid; or
methyl- or ethyl esters of vegetable oils such as rapeseed oil methyl ester or corn oil methyl ester.

Mixtures of aforementioned solvents are also possible. The water-immiscible solvent A is usually commerically available, such as the hydrocarbons under the tradenames Solvesso® 200, Aromatic® 200, or Caromax® 28. The aromatic hydrocarbons may be used as naphthalene depleted qualities.

Preferred solvents A are hydrocarbons, in particular aromatic hydrocarbons.

Preferably, solvent A has a solubility in water of up to 20 g/l at 20° C., more preferably of up to 5 g/l and in particular of up to 0.5 g/l.

Usually, solvent A has a boiling point above 100° C., preferably above 150° C., and in particular above 180° C.

The aprotic, polar solvent B has a solubility in water from 0.5 to 20 g/l at 20° C. Preferably, solvent B has a solubility in water from 0.5 to 10.0 g/l, in particular from 0.5 to 5.0 g/L. Mixtures of different kinds of solvent B are also possible. Preferably, solvent B is a ketone, which has a solubility in water from 0.5 to 20 g/l at 20° C. More preferably, solvent B is a ketone, which comprises from 6 to 18 (preferably from 7 to 16) C-atoms, and which has a solubility in water from 0.5 to 20 g/l at 20° C. Especially preferred as solvent B are 2-heptanone and/or acetophenone. In particular, solvent B is 2-heptanone. Preferably, solvent B is free of carbon-carbon double and/or triple bonds to avoid side reactions. Mixtures of aforementioned solvents are also possible.

For example, some solubility values are listed (all data at 20° C.): acetophenon 5.5 g/l, 2-Heptanon 4.3 g/l, 3-heptanone (2.6 g/l), 2-hexanone (14 g/l), 5-methyl-2-hexanone (5.4 g/l), 5-methyl-3-heptanone (3.0 g/l), 3-methyl-2-hexanone (4.1 g/l), 4-methyl-2-hexanone (4.3 g/l), 2-methyl-3-hexanone (6.3 g/l), 4-methyl-3-hexanone (5.2 g/l), 5-methyl-3-hexanone (5.2 g/l), 3-ethyl-2-pentanone (4.6 g/l), 3,3-dimethyl-2-pentanone (7.3 g/l), 3,4-dimethyl-2-pentanone (6.7 g/l), 4,4-dimethyl-2-pentanone (10.4 g/l), 2,2-dimethyl-3-pentanone (10.4 g/l), 2,4-dimethyl-3-pentanone (5.7 g/l), 2-octanone (0.9 g/l), 2,5-dimethyl-3-hexanone (2.6 g/l), 2,2-dimethyl-3-hexanone (2.8 g/l), 3,3-dimethyl-2-hexanone (2.7 g/l), 3,4-dimethyl-2-hexanone (1.4 g/l), 4,4-dimethyl-3-hexanone (2.5 g/l), 3-ethyl-4-methyl-2-pentanone (1.7 g/l), 2-methyl-3-heptanone (1.4 g/l), 2-methyl-4-heptanone (1.7 g/l), 3-methyl-2-heptanone (0.9 g/l), 3-methyl-4-heptanone (1.9 g/l), 5-methyl-3-heptanone (1.1 g/l), 6-methyl-2-heptanone (0.8 g/l), 6-methyl-3-heptanone (0.9 g/l), 3-octanone (0.8 g/l), 4-octanone (1.0 g/l), 2,2,4-trimethyl-3-pentanone (5.5 g/l), 3-ethyl-3-methyl-2-pentanone (1.8 g/l), 5-methyl-2-heptanone (1.0 g/l), isoporone (15 g/l).

Not suitable for use as solvent B are for example acetone (completely miscible with water), cyclohexanone (24 g/l), methylethylketone (353 g/l), or benzophenone (<0.005 g/l).

The core may contain further solvents in addition to solvent A and solvent B. Usually, the core comprises less than 40 wt %, preferably less than 20 wt %, and in particular less than 5 wt % of further solvents, based on the total weight of all solvents in the core.

Capsules with encapsulation material comprising polyurea are well known and can be prepared by analogy to prior art. They are preferably prepared by an interfacial polymerization process of a suitable polymer wall forming material, such as a polyisocyanate and a polyamine. Interfacial polymerization is usually performed in an aqueous oil-in-water emulsion or suspension of the core material containing dissolved therein at least one part of the polymer wall forming material. During the polymerization, the polymer segregates from the core material to the boundary surface between the core material and water thereby forming the wall of the microcapsule. Thereby an aqueous suspension of the microcapsule material is obtained. Suitable methods for interfacial polymerization processes for preparing microcapsules containing pesticide compounds have been disclosed in prior art.

In general, polyurea is formed by reacting a polyisocyanate having at least two isocyanate groups with a polyamine having at least two primary amino groups to form a polyurea wall material. In a further embodiment, the polyurea may be formed by contacting polyisocyanate with water. Preferably, the polyurea shell contains a polyisocyanate and a polyamine in polycondensed form. Suitable polyisocyanates are known, e.g. from US 2010/0248963 A1, paragraphs [0132] to [0158], to which full reference is made. Suitable polyamines are known, e.g. from US 2010/0248963 A1, paragraphs [0159] to [0169], to which full reference is made.

Polyisocyanates may be used individually or as mixtures of two or more polyisocyanates. Suitable polyisocyanates are for example aliphatic isocyanates or aromatic isocyanates. These isocyanates may be present as monomeric or oligomeric isocyanates. The NCO content may be determined according to ASTM D 5155-96 A.

Examples of suitable aliphatic diisocyanates include tetramethylene diisocyanate, pentamethylene diisocyanate and hexamethylene diisocyanate as well as cycloaliphatic isocycantates such as isophoronediisocyanate, 1,4-bisisocyanatocyclohexane and bis-(4-isocyanato-cyclohexyl)methane.

Suitable aromatic isocyanates include toluene diisocyanates (TDI: a mixture of the 2,4- and 2,6-isomers), diphenylmethene-4,4'-diisocyanate (MDI), polymethylene polyphenyl isocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4',4"-triphenylmethane triisocyanate. Also suitable are higher oligomers of the aforementioned diisocyanates such as the isocyanurates and biurethes of the aforementioned diisocyanates and mixtures thereof with the aforementioned diisocyanates.

In another preferred embodiment, the polyisocyanate is an oligomeric isocyanates, preferably an aromatic, oligomeric isocyanate. Such oligomeric isocyanates may comprise above mentioned aliphatic diisocyanates and/or aromatic isocyanates in oligomerized form. The oligomeric isocyanates have an average functionality in the range of 2.0 to 4.0, preferably 2.1 to 3.2, an more preferably 2.3 to 3.0. Typically, these oligomeric isocyanates have a viscosity (determined according to DIN 53018) in the range from 20 to 1000 mPas, more preferably from 80 to 500 mPas and especially from 150 to 320 mPas. Such oligomeric isocyanates are commercially available, for example from BASF SE under the tradenames Lupranat® M10, Lupranat® M20, Lupranat® M50, Lupranat® M70, Lupranat® M200, Lupranat® MM103 or from Bayer AG as Basonat® A270.

Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol and mixtures thereof with the aforementioned diisocyanates. In this way, several molecules of diisocyanate are linked through urethane groups to the polyhydric alcohol to form high molecular weight polyisocyanates. A particularly suitable product of this kind, DESMODUR® L (Bayer Corp., Pittsburgh), can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol.

Preferred polyisocyanates are isophorone diisocyanate, diphenylmethane-4,4'-diisocyanate, toluene diisocyanates, and oligomeric isocyanates, whereas oligomeric isocyanates are in particular preferred.

Suitable polyamines within the scope of this invention will be understood as meaning in general those compounds that contain two and more amino groups in the molecule, which amino groups may be linked to aliphatic or aromatic moieties.

Examples of suitable aliphatic polyamines are $\alpha,\omega$-diamines of the formula $H_2N-(CH_2)_n-NH_2$, wherein n is an integer from 2 to 6. Exemplary of such diamines are ethylenediamine, propylene-1,3-diamine, tetramethylenediamine, pentamethylenediamine and hexame-thylenediamine. A preferred diamine is hexamethylenediamine. Further suitable aliphatic polyamines are polyethylenimines of the formula $H_2N-(CH_2-CH_2-NH)_n-H$, wherein n is an integer from 2 to 20, preferably 3 to 5. Representative examples of such polyethylenimines are diethylenetriamine, triethylenetetramine, tetraethylenepentamine and pentaethylenehexamine. Further suitable aliphatic polyamines are dioxaalkane-$\alpha,\omega$-diamines, such as 4,9-dioxadodecane-1,12-diamine of the formula $H_2N-(CH_2)_3O-(CH_2)_4O-(CH_2)_3-NH_2$.

Examples of suitable aromatic polyamines are 1,3-phenylenediamine, 2,4- and 2,6-toluenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraminoanthraquinone. Those polyamines which are insoluble or insufficiently soluble in water may be used as their hydrochloride salts.

Polyamines, such as those mentioned above may be used individually or as mixtures of two or more polyamines. Preferred polyamine is a polyethylenimine, such as tetraethylenepentamine.

The relative amounts of each complementary wall-forming component will vary with their equivalent weights. In general, approximately stoichiometric amounts are preferred, while an excess of one component may also be employed, especially an excess of polyisocyanate. The total amount of wall-forming components approximately corresponds to the total amount of polymeric wall-forming materials.

The average particle size of the capsules (z-average by means of light scattering; preferably a $D_{4,3}$ average) is 0.5 to 50 μm, preferably 0.5 to 20 μm, more preferably 1 to 10 μm, and especially 1 to 8 μm.

The term pesticides refers to at least one active substance selected from the group of the fungicides, insecticides, nematicides, herbicides, safeners and/or growth regulators. Preferred pesticides are fungicides, insecticides, herbicides and growth regulators. Especially preferred pesticides are insecticides. Mixtures of pesticides of two or more of the abovementioned classes may also be used. The skilled worker is familiar with such pesticides, which can be found, for example, in the Pesticide Manual, 15th Ed. (2009), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

The pesticide comprises preferably an insecticide, in particular alphacypermethrin.

The pesticide has preferably a solubility in water of less than 10 g/l at 20° C. More preferably, it has solubility of less than 1.0 g/l, in particular of less than 0.2 g/l. For example, the solubilities in water are: pyraclostrobin 1.9 mg/l, prochloraz 34 mg/L, metrafenon 0.5 mg/l, alphacypermethrin 0.01 mg/l.

The pesticide has usually a solubility in a mixture of aromatic hydrocarbons with a distillation range of 235-290° C. (e.g. Solvesso® 200 ND) and 2-heptanon (1:1 wt %) of at least 10 wt %, preferably at least 20 wt %, and in particular at least 30 wt %, at 20° C.

The pesticide has usually a melting point of at least 30° C., preferably at least 40° C., and in particular at least 45° C. For example the melting points are: pyraclostrobin 64° C., prochloraz 47° C., metrafenon 100° C., alphacypermethrin 79° C.

The pesticide may be present in the core dissolved form, as suspension, emulsion or suspoemulsion. Preferably, the pesticide is present in dissolved form.

The weight ratio of the pesticide in the core (or of the sum of all pesticides in case more than one pesticide is present in the core) to the sum of all solvents (e.g. solvent A and solvent B) in the core is typically from 5:1 to 1:20, preferably from 1:1 to 1:10, more preferably from 1:1.2 to 1:5, and in particular from 1:1.5 to 1:3.

The core contains at least 5 wt %, preferably at least 15 wt % and in particular at least 25 wt % of pesticide, based on the total amount of the core materials. The core may contain up to 70 wt %, preferably up to 50 wt % of pesticide. The amount of core materials is typically summed up from the amounts of all pesticides and solvents in the core.

The core contains at least 10 wt %, preferably at least 20 wt % and in particular at least 35 wt % of solvent A, based on the total amount of the core materials. In another preferred form, the core contains at least 25 wt % solvent A, based on the total amount of the core materials. The core may contain up to 90 wt %, preferably up to 70 wt % of solvent A. In another preferred form, the core may contain up to 55 wt %, preferably up to 45 wt % of solvent A.

The core contains at least 5 wt %, preferably at least 10 wt % and in particular at least 18 wt % of solvent B, based on the total amount of the core materials. In another preferred form, the core contains at least 25 wt %, preferably at least 30 wt % solvent B, based on the total amount of the core materials The core may contain up to 80 wt %, preferably up to 65 wt % of solvent B. In another preferred form, the core may contain up to 55 wt %, preferably up to 45 wt % of solvent B The weight ratio of solvent A to solvent B is usually in the range from 5:95 to 95:5, preferably from 10:1 to 1:5, more preferably from 5:1 to 1:2, and in particular from 3:1 to 1:1. In another preferred form, the weight ratio of solvent A to solvent B is usually in the range from 5:1 to 1:5, preferably from 3:1 to 1:2, more preferably from 2:1 to 1:2.

The core may optionally contain auxiliaries, such as those mentioned below. Preferably, the core contains at least one adjuvant (for example organic modified polysiloxanes such as Break Thru S 240®; alcohol alkoxylates such as Atplus 245®, Atplus MBA 1303°, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®).

The microcapsules contains up to 15 wt %, preferably up to 10 wt % and in particular up to 6 wt % of shell (e.g. based on the total amount of pesticide, all solvents in the core (preferably solvent A and solvent B), polyisocyate, and polyamine). The microcapsules contain usually at least 0.5 wt %, preferably at least 1.5 wt % shell.

The present invention further relates to a method for preparing the microcapsules according to the invention, comprising the step of mixing an oil phase and a water phase, wherein the oil phase comprises the pesticide, the solvent A, the solvent B, and the polyisocyanate. Typically, the water phase contains the polyamine. Usually, the mixture is heated to at least 50° C., preferably to at least 60° C.

The present invention further relates to an aqueous composition comprising the microcapsules according to the invention. Preferably, this composition comprises a non-encapsulated pesticide. This non-encapsulated pesticide may be present in dissolved form, or as a suspension, emulsion or suspoemulsion. It may be identical or different to the pesticide in the core. The aqueous composition contains usually from 5 to 80 wt % of the microcapsules, preferably from 10 to 60 wt %. The aqueous composition contains usually at least 2 wt % encapsulated pesticide, preferably at least 5 wt % and in particular at least 8 wt %. Typically, the composition comprises from 0.5 to 25 wt %, preferably from 1.0 to 20 wt % and in particular from 2.0 to 15 wt % surface-active substances. Suitable surface-active substances are listed below. Specific examples are Atlas® G 5000, Tween® 20, Soprophor® 796 P, Soprophor® FLK, Soprophor® 4D 384, Soprophor® S 25, Soprophor® BSU, Pluronic® PE 6400, Pluronic® PE 6800, Pluronic® PE 10500, Luviskol® VA 64, Luvitek® K30, Lutensol® TO 10, Lutensol® ON 70, Emulsogen® 35010.

The aqueous compositions according to the invention may also comprise auxiliaries which are customary in agrochemical formulations. The auxiliaries used depend on the particular application form and active substance, respectively. Examples for suitable auxiliaries are dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable surface-active substances (adjuvants, wetters, stickers, dispersants or emulsifiers) are the alkali metal, alkaline earth metal and ammonium salts of aromatic sulfonic acids, for example of lingo- (Borresperse® types, Borregaard, Norway), phenol-, naphthalene- (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors, and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone, and their copolymers.

Surfactants which are particularly suitable are anionic, cationic, nonionic and amphoteric surfactants, block polymers and polyelectrolytes. Suitable anionic surfactants are alkali, alkaline earth or ammonium salts of sulfonates, sulfates, phosphates or carboxylates. Examples of sulfonates are alkylarylsulfonates, diphenylsulfonates, alpha-olefin sulfonates, sulfonates of fatty acids and oils, sulfonates of ethoxylated alkylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are alkoxylates, N-alkylated fatty acid amides, amine oxides, esters or sugar-based surfactants. Examples of alkoxylates are compounds such as alcohols, alkylphenols, amines (e.g. tallow amine), amides, arylphenols, fatty acids or fatty acid esters which have been alkoxylated. Ethylene oxide and/or propylene oxide may be employed for the alkoxylation, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide or of the A-B-C type comprising alkanol, polyethylene oxide and polypropylene oxide. Suitable polyelectrolytes are polyacids or polybases. Examples of polyacids are alkali salts of polyacrylic acid. Examples of polybases are polyvinylamines or polyethyleneamines.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopolo 23 (Rhodia, France), Veegum® (R.T. Vanderbilt, U.S.A.) or Attaclay® (Engelhard Corp., NJ, USA). Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof. Examples for tackifiers or binders are polyvinylpyrrolidons, polyvinylacetates, polyvinyl alcohols and cellulose ethers (Tylose®, Shin-Etsu, Japan).

The present invention further relates to a method for controlling phytopathogenic fungi and/or undesired plant growth and/or undesired attack by insects or mites and/or for regulating the growth of plants, where the microcapsules or the aqueous composition according to the invention is allowed to act on the particular pests, their habitat or the plants to be protected from the particular pest, the soil and/or on undesired plants and/or the useful plants and/or their habitat.

Various cultivated plants my be treated, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broadleaved trees or evergreens, e.g. conifers; and on the plant propagation material, such as seeds, and the crop material of these plants.

In the sense of the present invention, "insects or mites" are preferably selected from arthropods and nematodes, more preferably from harmful insects, arachnids and nematodes, and even more preferably from insects, acarids and nematodes, wherein insects are most preferred. Examples are insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani* and *Zeiraphera canadensis;* beetles (Coleoptera), for example *Agrilus sinuatus, Agriotes lineatus, Agriotes obscu-rus, Amphimallus solstitialis, Anisandrus dispar, Anthonomus grandis, Anthonomus pomorum, Atomaria linearis, Blastophagus piniperda, Blitophaga undata, Bruchus rufi-manus, Bruchus pisorum, Bruchus lentis, Byctiscus betulae, Cassida nebulosa, Cero-toma trifurcata, Ceuthorrhynchus assimilis, Ceuthorrhynchus napi, Chaetocnema tibi-alis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hip-pocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyl-lopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya homi-nivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destruc-tor, Musca domestica, Muscina stabulans, Oestrus ovis, Oscinella frit, Pegomya hyso-cyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, So-lenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melano-plus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus* telarius and *Tetranychus urticae, Panonychus ulmi, Panonychus citri*, and *oligonychus pratensis;* siphonatera, e.g. *Xenopsylla cheopsis, Ceratophyllus* spp.

Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the microcapsules or the compositions thereof, respectively, are applied on to the plant propagation material by a method such that germination is not induced, e.g. by seed dressing, pelleting, coating and dusting. In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The microcapsules or the aqueous composition can be used as such or in the form of their agrochemical formulations, e.g. in the form of directly sprayable solutions, suspensions, dispersions, emulsions, oil dispersions, by means of spraying, atomizing, dusting, spreading, brushing, immersing or pouring. The application forms depend entirely on the intended purposes; it is intended to ensure in each case the finest possible distribution of the pesticides. The active substance concentrations in the ready-to-use preparations can be varied within relatively wide ranges. In general, they are from 0.0001 to 10%, preferably from 0.001 to 1% by weight of active substance. The active substances may also be used successfully in the ultra-low-volume process (ULV), it being possible to apply compositions comprising over 95% by weight of active substance, or even to apply the active substance without additives.

When employed in plant protection, the amounts of active substances (also called pesticide) applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the aqueous compositions, if appropriate not until immediately prior to use (tank mix). These agents can be admixed with the compositions according to the invention in a weight ratio of 1:100 to 100:1, preferably 1:10 to 10:1. Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The present invention further relates to microcapsules comprising a shell and a core, which contains contains a pesticide and 2-heptanone. Preferably, the shell is a polyurea shell. Suitable examples for a polyurea shell and for a pesticide are described above.

The present invention has various advantages: The invention reduces the crystallization of the active ingredients; it increases the stability of the formulation within broad range of temperatures; there is a knock-down as well as a residual efficacy; it improves compatibility with other pesticides; it reduces the wind drift; the encapsulated active ingredients are effectively protected from UV-light; the capsules may be loaded with both oil and water soluble active ingredients and adjuvants; the capsules have a increased rainfastness; there is a reduced toxicological effect for the worker and users; the formulation is very stable against UV-light or sunlight; the capsules have a high physical stability; the formulation has a excellent biodelivery; the formulation has a very low toxicology (e.g. no eye irritation)); the formulation has a low contact angle of the sprayed drops on leaves; the formulation has a high spreading on leaves.

The examples below give further illustration of the invention, which is not, however, restricted to these examples.

EXAMPLES

MDI based polyisocyanate: solvent free polyisocyanate based on 4,4'-diphenylmethane diisocyanate (MDI) with an average functionality of 2.7, NCO content 32 g/100 g.

Aromatic hydrocarbon A: Aromatic hydrocarbon solvent, distillation range 240-295° C., freezing point −10 to −20° C., naphthalene content below 1 wt %.

Aromatic hydrocarbon B: Aromatic hydrocarbon solvent, distillation range 175-215° C., freezing point −20 to −25° C., naphthalene content below 1 wt %.

PVA: Partially hydrolyzed polyvinyl alcohol, viscosity 17-19 mPas (DIN 53015).

UV-Absorber: 2-Hydroxy-4-octoxybenzophenone

Example 1

Preparation of Capsules

| Aqueous phase: | |
|---|---|
| 583 g | water |
| 395 g | 10 wt % aqueous solution of polyvinylalkohol PVA |
| Oil phase: | |
| 313 g | alpha-cypermethrin |
| 418 g | Aromatic hydrocarbon A |
| 209 g | 2-heptanon |
| 28 g | MDI based polyisocyanate |
| Feed 1: | |
| 13 g | tetraethylenpentamine |
| 49 g | water |

The oil phase was added to the aqueous phase and dispersed for 20 min with a dissolver stirrer at 6000 rpm. Then feed 1 was added in 15 min and the emulsion was heated for 2 h at 80° C. After cooling to room temperature a suspension of capsules was obtained with a solid content of 49%. The average particle size D[4,3] was 2.5 μm. The percentage of evaporation (2 h 105° C., 1 h 130° C.) was 2%.

Example 2

Preparation of Capsules

| | Aqueous phase: |
|---|---|
| 183 g | water |
| 116 g | 10 wt % aqueous solution of polyvinylalkohol PVA |
| | Oil phase: |
| 91 g | alpha-cypermethrin |
| 122 g | Aromatic hydrocarbon A |
| 61 g | 2-Heptanone |
| 11 g | MDI based polyisocyanate |
| 10 g | UV-Absorber |
| | Feed 1: |
| 5 g | tetraethylenpentamine |
| 14 g | water |

The oil phase was added to the aqueous phase and dispersed for 20 min with a dissolver stirrer at 6000 rpm. Then feed 1 was added in 15 min and the emulsion was heated for 2 h at 80° C. After cooling to room temperature a suspension of capsules was obtained with a solid content of 49%. The average particle size D[4,3] was 2.2 μm.

Example 3

Preparation of Capsules

| | Aqueous phase: |
|---|---|
| 139 g | water |
| 88 g | 10 wt % aqueous solution of polyvinylalkohol PVA |
| | Oil phase: |
| 69 g | alpha-cypermethrin |
| 92 g | Aromatic hydrocarbon B |
| 46 g | Acetophenone |
| 8 g | MDI based polyisocyanate |
| 17 g | UV-Absorber |
| | Feed 1: |
| 4 g | Tetraethylenpentamine |
| 11 g | water |

The oil phase was added to the aqueous phase and dispersed for 20 min with a dissolver stirrer at 6000 rpm. Then feed 1 was added in 15 min and the emulsion was heated for 2 h at 80° C. After cooling to room temperature a suspension of capsules was obtained with a solid content of 49%. The average particle size D[4,3] was 2.6 μm.

Example 4

Preparation of Capsules

| | Aqueous phase: |
|---|---|
| 149 g | water |
| 92 g | 10 wt % aqueous solution of polyvinylalkohol PVA |
| | Oil phase: |
| 74 g | alpha-cypermethrin |
| 98 g | Aromatic hydrocarbon A |
| 49 g | 2-Heptanon |
| 9 g | MDI based polyisocyanate |
| | Feed 1: |
| 4 g | Diethylentriamine |
| 12 g | water |

The oil phase was added to the aqueous phase and dispersed for 20 min with a dissolver stirrer at 6000 rpm. Then feed 1 was added in 15 min and the emulsion was heated for 2 h at 80° C. After cooling to room temperature a suspension of capsules was obtained with a solid content of 49%. The average particle size D[4,3] was 3.0 μm.

Example 5

Preparation of Capsules

| | Aqueous phase: |
|---|---|
| 192 g | water |
| 120 g | 10 wt % aqueous solution of polyvinylalkohol PVA |
| | Oil phase: |
| 96 g | alpha-cypermethrin |
| 128 g | Aromatic hydrocarbon A |
| 64 g | 2-Heptanon |
| 12 g | MDI based polyisocyanate |
| | Feed 1: |
| 3 g | Tetraethylenpentamine |
| 15 g | water |

The oil phase was added to the aqueous phase and dispersed for 20 min with a dissolver stirrer at 2000 rpm. Then feed 1 was added in 15 min and the emulsion was kept for 2 h at 20° C. Then it was heated for 2 h at 60° C. After cooling to room temperature a suspension of capsules was obtained with a solid content of 49%. The average particle size D[4,3] was 7.2 μm.

Example 6

Preparation of Capsules

| | Aqueous phase: |
|---|---|
| 223 g | water |
| 58 g | 10 wt % aqueous solution of polyvinylalkohol PVA |
| | Oil phase: |
| 94 g | alpha-cypermethrin |
| 125 g | Aromatic hydrocarbon A |
| 63 g | 2-Heptanon |
| 8 g | MDI based polyisocyanate |
| | Feed 1: |
| 4 g | Tetraethylenpentamine |
| 15 g | water |

The oil phase was added to the aqueous phase and dispersed for 20 min with a dissolver stirrer at 6000 rpm. Then feed 1 was added in 15 min and the emulsion was heated for 2 h at 80° C. After cooling to room temperature a suspension of capsules was obtained with a solid content of 49%. The average particle size D[4,3] was 2.9 µm.

Example 7

Preparation of Capsules

| | Aqueous phase: |
|---|---|
| 335 g | water |
| 104 g | 10 wt % aqueous solution of polyvinylalkohol PVA |
| | Oil phase: |
| 154 g | alpha-cypermethrin |
| 175 g | Aromatic hydrocarbon A |
| 175 g | 2-heptanon |
| 15 g | MDI based polyisocyanate |
| | Feed 1: |
| 7 g | tetraethylenpentamine |
| 25 g | water |

The oil phase was added to the aqueous phase and dispersed for 20 min with a dissolver stirrer at 3500 rpm. Then feed 1 was added in 15 min and the emulsion was heated up for 1 h to 80° C. and kept at this temperature for 2 h. After cooling to room temperature a suspension of capsules was obtained with a solid content of 54%. The average particle size D[4,3] was 2.9 µm.

Examples 8-14

The details are pointed out in table 1 and were made comparable to examples 1-7.

TABLE 1

| Example | Comparable to Example | Differences | Solid content | Particle size D[4.3] |
|---|---|---|---|---|
| 8 | 2 | 22 g UV-Absorber instead of 10 g | 50% | 2.3 µm |
| 9 | 2 | 30 g UV-Absorber instead of 10 g | 51% | 2.4 µm |
| 10 | 3 | 23 g UV-Absorber instead of 17 g | 47% | 2.6 µm |
| 11 | 4 | Isophorondiisocyanat instead of MDI based polyisocyanate | 50% | 2.7 µm |
| 12 | 6 | It was dispersed for 20 min with a dissolver stirrer at 4000 rpm instead of 6000 rpm | 49% | 4.8 µm |
| 13 | 6 | It was dispersed for 20 min with a dissolver stirrer at 2500 rpm instead of 6000 rpm | 49% | 6.3 µm |
| 14 | 1 | The emulsion was heated for 2 h at 90° C. instead of 80° C. | 49% | 2.0 µm |

Example 15

Preparation of Agrochemical CS Formulation

A) The capsules raw suspension of example 1 was mixed with water and additives while stirring at room temperature. Thus, an aqueous CS agrochemical formulation was obtained containing 31.5 wt % of the capsule raw suspension, 0.1 wt % antifoam, 0.2 wt % preservative, 10.0 wt % propylene glycol antifreeze, 8 wt % nonionic alkylalkoxylates surfactants, 0.1 wt % xanthan gum and water up to 100%.

B) The capsules raw suspension of example 2 was mixed with water and additives while stirring at room temperature. Thus, an aqueous CS agrochemical formulation was obtained containing 10 wt % of the encapsulated alphacypermethrin, 0.1 wt % antifoam, 0.2 wt % preservative, 10.0 wt % propylene glycol antifreeze, 3 wt % nonionic alkylalkoxylates surfactant and water up to 100 wt %.

Example 16

Storage Stability

Samples of the capsule formulation of example 15B were used for storage tests.

For comparison, a capsule suspension was prepared as in example 15B, wherein the 2-heptanone was substituted by cyclohexanone. All other components remained the same.

Samples of both formulations were stored for two weeks either at −10° C. or at +54° C.

Results of the visual inspection: There was no sediment observable after two weeks in the samples of example 15B. However, in the comparative samples with cyclohexanone sediment and serum were clearly observable.

We claim:

1. Microcapsules comprising a polyurea shell and a core, which contains a pesticide, a water-immiscible solvent A and at least 5 wt % of an aprotic, polar solvent B, based on the total weight of the solvents in the core,
   wherein the pesticide has a solubility in water of less than 10 g/l at 20° C.,
   wherein solvent A is a hydrocarbon, a vegetable oil, a fatty acid ester, a methyl- or ethyl ester of vegetable oil, or a mixture of the aforementioned solvents,
   wherein solvent B is 2-heptanone; and
   wherein the weight ratio of solvent A to solvent B is in the range from 3:1 to 1:2.

2. The microcapsules according to claim 1, wherein the pesticide is present in dissolved form.

3. The microcapsules according to claim 1 containing from 1.5 to 10 wt % of the shell.

4. The microcapsules according to claim 1, wherein the polyurea shell contains a polyisocyanate and a polyamine in polycondensed form.

5. The microcapsules according to claim 4, wherein the polyamine comprises a polyethyleneamine.

6. The microcapsules according to claim 1, wherein solvent A is a hydrocarbon.

7. The microcapsules according to claim 1, wherein weight ratio of the pesticide to the sum of all solvents in the core is from 1:1 to 1:10.

8. Microcapsules comprising a shell and a core, which contains a pesticide and 2-heptanone, wherein the shell is a polyurea shell, and wherein the pesticide has a solubility in water of less than 10 g/l at 20° C.

9. A method for preparing the microcapsules as defined in claim 1, comprising the step of mixing an oil phase and a water phase, wherein the oil phase comprises the pesticide, the solvent A, the solvent B, and a polyisocyanate.

10. An aqueous composition comprising the microcapsules as defined in claim 1.

11. The composition according to claim 10, comprising a non-encapsulated pesticide.

12. A method for controlling phytopathogenic fungi and/or undesired plant growth and/or undesired attack by insects or mites and/or for regulating the growth of plants, wherein a composition comprising the microcapsules as defined in claim 1 is allowed to act on the particular pests, their habitat or the plants to be protected from the particular pest, the soil and/or on undesired plants and/or the useful plants and/or their habitat.

13. The method of claim 12, wherein the pesticide is present in dissolved form.

14. The method of claim 12, wherein the microcapsules contain from 1.5 to 10 wt % of the shell.

* * * * *